United States Patent

Harrington et al.

[11] Patent Number: 5,837,116
[45] Date of Patent: Nov. 17, 1998

[54] TWO DIMENSIONAL ELECTROPHORESIS APPARATUS

[75] Inventors: Michael G. Harrington; Douglas Packard, both of La Canada, Calif.

[73] Assignee: California Institute of Technology, Pasadena, Calif.

[21] Appl. No.: 691,001

[22] Filed: Jul. 12, 1996

[51] Int. Cl.[6] .................................................. G01N 27/26
[52] U.S. Cl. ............................................................ 204/606
[58] Field of Search ................................... 204/456, 459, 204/466, 450, 600, 606, 616

[56] References Cited

U.S. PATENT DOCUMENTS

4,385,974  5/1983  Shevitz ................................ 204/180 G

*Primary Examiner*—Kathryn L. Gorgos
*Assistant Examiner*—Alex Noguerda
*Attorney, Agent, or Firm*—Oppenheimer, Wolff & Donnelly LLP

[57] ABSTRACT

A two dimensional electrophoresis apparatus which includes a first dimension electrophoresis box assembly which is connected to second dimension electrophoresis box assembly to provide two dimensional electrophoresis of proteins, peptides, DNA/RNA and related materials. The apparatus is designed for use in conducting two dimensional electrophoresis where isoelectric focusing is carried out in a first dimension to provide separation of samples based on charge followed by polyacrylamide gel electrophoresis as a second dimension wherein the sample bands resulting from the first dimension electrophoresis are separated according to mass. The apparatus may also be used in conducting other two dimensional electrophoresis procedures based on combinations of other gels.

15 Claims, 4 Drawing Sheets

TWO DIMENSIONAL ELECTROPHORESIS APPARATUS

The U.S. Government has certain rights in this invention pursuant to Grant No. 8809710 awarded by the National Science Foundation.

BACKGROUND OF THE INVENTION

1. Field of the Invention

The present invention relates generally to two dimensional electrophoresis of proteins, peptided DNA/RNA and other related substances. More particularly, the present invention relates to the equipment which is specifically designed for use in conducting two dimensional electrophoresis.

2. Description of Related Art

High resolution two-dimensional gel electrophoresis (2DE) of proteins first became widely used in the mid to late 1970's. The popularity of 2DE is due principally to the methods ability to separate complex protein mixtures based on two independent variables, i.e. charge and mass. The first dimension of the two-dimensional gel electrophoresis method involves isoelectric focusing (IEF). As is well known, IEF provides separation based principally upon charge. The second dimension of the electrophoresis process is based on sodium dodecyl sulfate-polyacrylamide gel electrophoresis (SDS-PAGE) which provides separation based principally upon mass.

Subjecting a sample to the combined resolving powers of IEF followed by SDS-PAGE provides high resolution system where more than 7,500 proteins can be purified from an original source material. 2DE is also well-suited for use in separating complex mixtures of peptides and mixtures of DNA and/or RNA.

The apparatus used to conduct two-dimensional electrophoresis plays an important part in determining the overall effectiveness of the method. Widespread use and acceptance of this extremely useful separation procedure is dependent in part upon the ability to provide an apparatus which is well-suited for use by technicians in clinical laboratory settings. For example, the 2DE apparatus must be sufficiently versatile that it can be easily modified to meet differing laboratory needs. The apparatus should also be relatively simple so that quick and easy cleaning, inspection and repair can be accomplished.

A number of different steps must be followed in carrying out two dimensional electrophoresis. These steps include initial preparation of the IEF gel for first dimension electrophoresis and preparation of the polyacrylamide gel for the second dimensional electrophoresis. Other steps in the 2DE method include application of sample to the IEF gel, circulation of appropriate buffers through the system, application of appropriate voltages and control of temperatures. In order for an apparatus to function appropriately, it must include systems which provide for all of these various functions.

In addition to the above-described basic functions, it would be desirable to provide a two-dimensional electrophoresis apparatus which includes additional features. For example, it would be desirable to provide an apparatus wherein standard samples may be applied along the edges of the second dimension electrophoresis gel to assist in sample identification. As another example, it would be desirable to provide for the addition of various chemical reactants to the first dimensional electrophoresis gel during or after electrophoresis. Also, it would be desirable to provide an apparatus wherein an automated system is provided for sequentially conducting second dimensional electrophoresis on a series of gels containing samples which have already undergone first dimension electrophoresis.

In view of the above, it is apparent that there is a present and continuing need to provide 2DE apparatus with new and improved features which are useful in conducting two dimensional electrophoresis of proteins and other substances amenable to separation by charge and mass.

SUMMARY OF THE INVENTION

In accordance with the present invention, a two dimensional electrophoresis apparatus is provided which is well suited for use in clinical laboratory settings. The two dimensional electrophoresis apparatus of the present invention is a versatile device which includes features that allow for conducting a full range of two dimensional electrophoresis procedures.

The apparatus includes a first dimension electrophoresis box assembly in which first dimension electrophoresis is conducted. This first dimension electrophoresis box assembly includes a first dimension housing which has an upstream end at which the sample is located prior to electrophoresis and a downstream end toward which the sample migrates during electrophoresis. The first dimension housing includes a longitudinal first dimension electrophoresis zone which extends from the upstream end of the housing to the downstream end.

The first dimension housing further includes a chamber which is designed to house the electrophoresis electrode for the second dimension electrophoresis. This chamber extends longitudinally parallel to the first dimension electrophoresis zone. The chamber is located in fluid communication with the first dimension electrophoresis zone so that the sample bands present in the first dimension electrophoresis gel may be electrophoretically migrated out of the first dimension gel into the second dimension gel. Migration is accomplished when an electric potential is applied between the second dimension electrophoresis electrode located in the chamber and the corresponding second dimension electrophoresis electrode located at the downfield end of the second dimension electrophoresis gel.

As a feature of the present invention, a liquid permeable gel support bar is located in the first dimension electrophoresis zone. The support bar extends from the upstream end to the downstream end of the first dimension housing and provides support for the first dimensional electrophoresis gel. As a further feature of the present invention, the gel support bar includes a longitudinal channel located directly beneath the first dimension electrophoresis gel to provide for the introduction of various reactive agents into contact with the gel before, after and during the first dimension electrophoresis.

The first dimension housing includes openings at both the upstream end and downstream end into which the electrode assemblies are inserted prior to electrophoresis. As a feature of the present invention, one of the first dimensional electrode assemblies includes a sample applicator which is designed to accurately introduce a sample aliquot onto the upstream end of the first dimension electrophoresis gel.

As further features of the present invention, fill pins are provided which have interior channels through which fluids, such as the gel precursors, may be introduced into the first dimension electrophoresis zone. The fill pins are designed for insertion into the same openings utilized in connection with the electrode assemblies. As an additional feature of the present invention, a second dimension standard sample pin is provided which may be inserted into one or both of the openings in the first dimension housing to provide application of a standard sample to the upstream end or downstream ends of the first dimension gel. The standard samples are then transferred to the lateral edges of the second dimension gel by electromigration during the second dimension electrophoresis.

A second dimension electrophoresis box assembly is provided which includes a second dimension housing having an upfield end located adjacent to the first dimension housing and a downfield end towards which the sample bands migrate during the second dimension electrophoresis. In accordance with the present invention, the first and second dimension housings are connected together in such a manner that the first dimension electrophoresis gel support surface is oriented so that the first dimension gel is coplanar with the second dimension electrophoresis gel which is located on at lest one support surface. The coplanar alignment of the support surfaces insures that the first dimension gel and second dimension gel are positioned relative each other so that the bands of separated sample are accurately transferred by electrophoretic migration from the first dimension gel to the second dimension gel during the start of second dimension electrophoresis.

As another feature of the present invention, the electrophoresis apparatus includes a system for sequentially connecting a plurality of first dimension housings to a single second dimension housing. Preferably, the second dimension gel is sandwiched between two support surfaces. The sequential connection system allows multiple first dimension electrophoresis runs to be conducted with the resulting separated samples in their respective first dimension gels being sequentially positioned adjacent to the second dimension electrophoresis housing for second dimension electrophoresis.

The two dimension electrophoresis apparatus in accordance with the present invention is a versatile piece of equipment which is well suited for use in clinical laboratories where a wide variety of proteins, peptides, DNA/RNA and other materials must be accurately and reproducibly separated and isolated.

The above discussed and many other features and attendant advantages of the present invention will become better understood by reference to the following detailed description when taken in conjunction with the accompanying drawings.

DESCRIPTION OF THE PREFERRED EMBODIMENTS

A preferred exemplary two dimensional electrophoresis apparatus in accordance with the present invention is shown generally at 10 in FIGS. 1–5. The apparatus 10 includes a first dimension electrophoresis box assembly 12 and a second dimension electrophoresis box assembly 14. The apparatus is designed to carry out two-dimensional electrophoresis of proteins, peptides, DNA/RNA and other materials amenable to separation by two-dimensional electrophoresis.

Exemplary two-dimensional electrophoresis procedures for which the apparatus is well-suited are set forth in an article entitled "Analytical and Micropreparative Two-Dimensional Electrophoresis of Proteins" by M. G. Harrington, D. Gudeman, T. Zewert, M. Yun, and L. Hood (METHODS: A Companion to Methods in Enzymology, Volume 3, No. 2, Oct. pp. 98–108, 1991). The contents of this reference, along with all of the references cited in the article are hereby incorporated by reference.

The first dimension electrophoresis box assembly 12 includes a first dimension housing 16 which has an upstream end 18 and a downstream end 20. The first dimension housing 16 is located within an outer shell 22 which holds it in place with respect to the second dimension box assembly 14.

Figure 1:
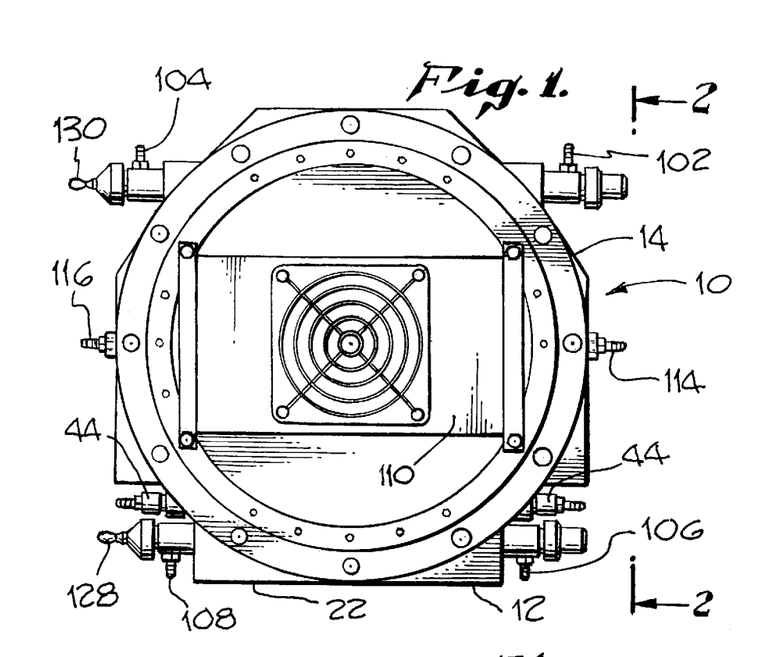
FIG. 1 is a top view of a preferred exemplary two dimensional electrophoresis apparatus in accordance with the present invention.
Figure 2:
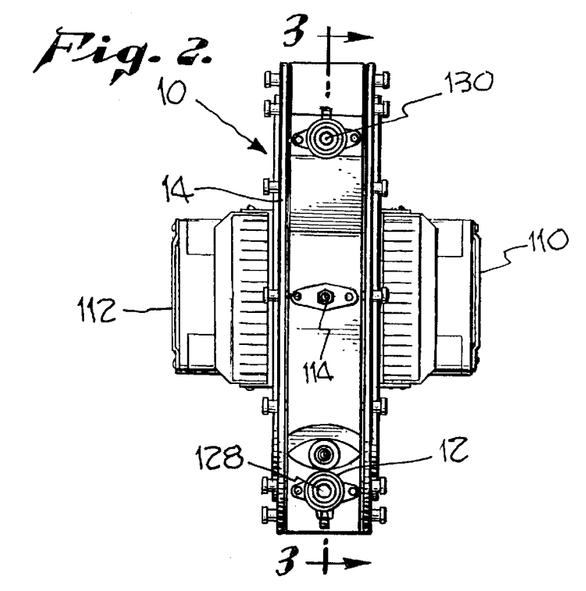
FIG. 2 is a side view of the two dimensional electrophoresis apparatus of FIG. 1 taken in the 2—2 plane.
Figure 3:
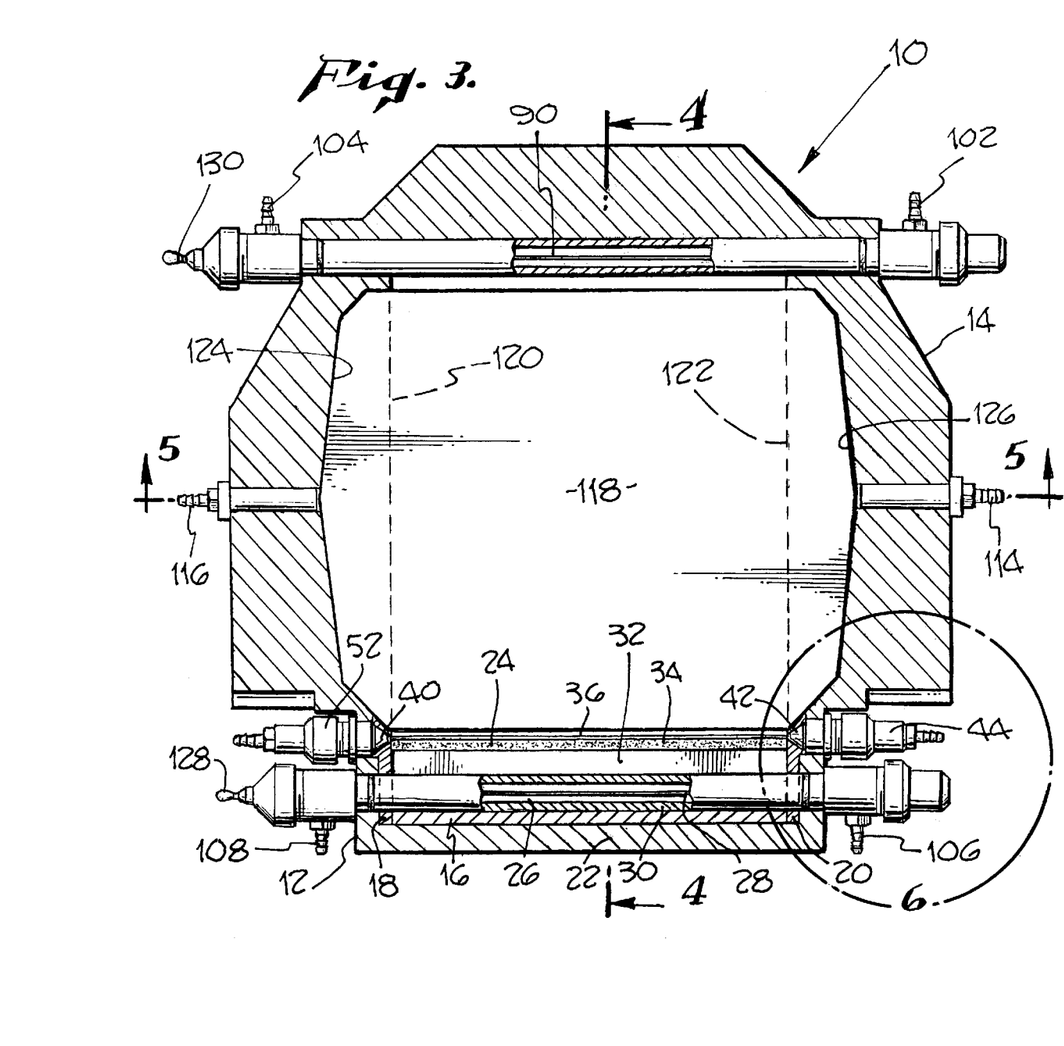
FIG. 3 is a sectional view of the preferred two dimensional electrophoresis apparatus taken in the 3—3 plane.
Figure 4:
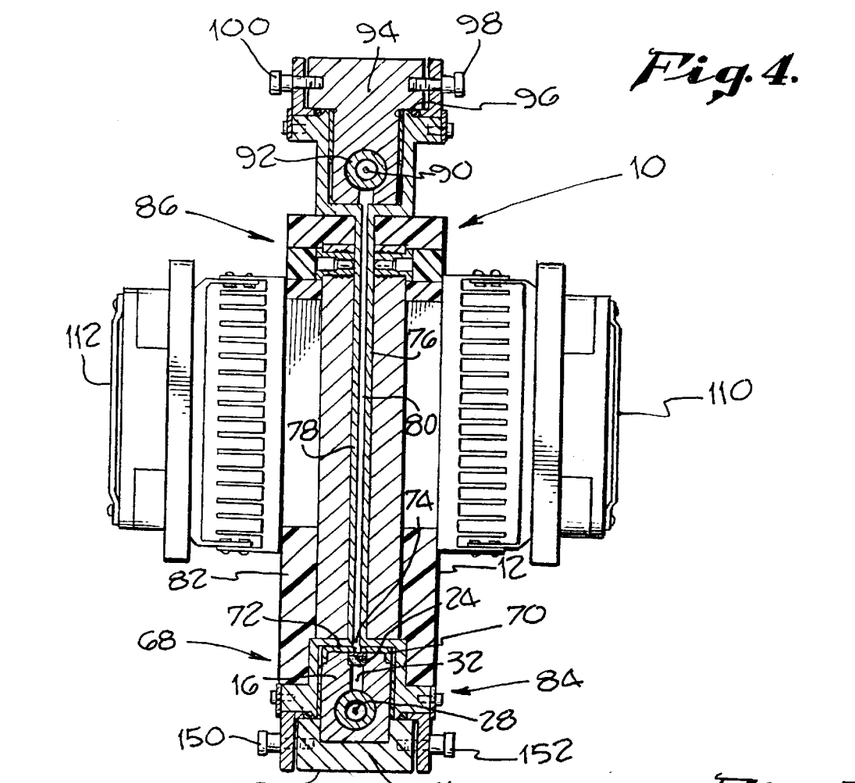
FIG. 4 is a sectional view of FIG. 3 taken in the 4—4 plane.
Figure 5:
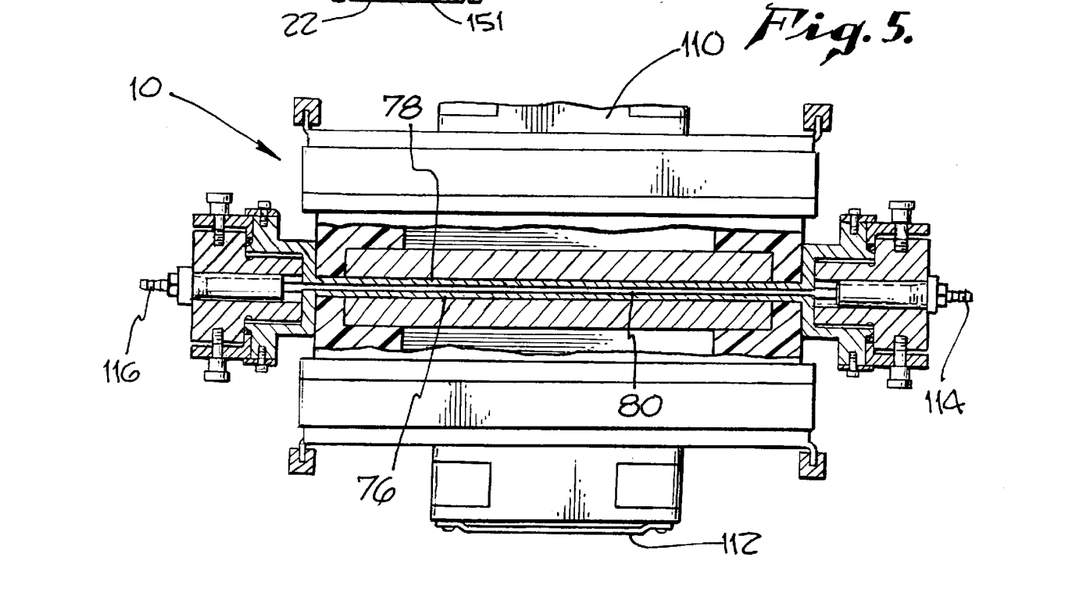
FIG. 5 is a sectional view of FIG. 3 taken in the 5—5 plane.

The first dimension housing 16 includes a first dimension electrophoresis zone 24 which extends from the upstream end 18 to the downstream end 20 of the first dimension housing 16. The first dimension housing 16 further includes a second dimension electrophoresis electrode chamber 26. An electrode 28 is located in chamber 26 for use in second dimension electrophoresis. A porous plastic tubular insert 30 surrounds electrode 28 to allow free flow of electrophoresis buffers into contact with the electrode 28. A longitudinal channel 32 extends the length of the first dimension housing 16 to provide fluid communication between the second dimension electrophoresis electrochamber 26 and the first dimension electrophoresis zone 24.

A liquid permeable gel support bar 34 is located within the first dimension electrophoresis zone 24 to provide support for the first dimension electrophoresis gel. A preferred exemplary first dimension electrophoresis gel is shown at 36. The first dimensional electrophoresis gel 36 may be any of the well known gels used for separation of materials by electrophoresis. Preferably, the gel will be of the type used in isoelectric focusing. As is well known, the various constituents present in a sample solution are separated during isoelectric focusing based principally on their charge.

In isoelectric focusing, the sample is applied to the upstream end of a gel and migrates towards the downstream end of the gel. During isoelectric focusing, the sample is separated into numerous bands which are present at spaced locations between the upstream and downstream ends of the gel. In describing the present invention, applicant has arbitrarily chosen the upstream and downstream ends for the first dimension electrophoresis housing. As is well known in the art, the upstream and downstream ends of the gel may be switched by appropriate changes in gel preparation and voltage application.

For example, as shown in FIG. 3, the upstream end of gel 36 is located on the left side of the apparatus with the downstream end being located on the right side of the apparatus. As a result, electrophoresis of the sample occurs from left to right in FIG. 3; however, if desired, the upstream and downstream ends of the gel may be reversed with electrophoresis occurring from right to left.

Figure 7:
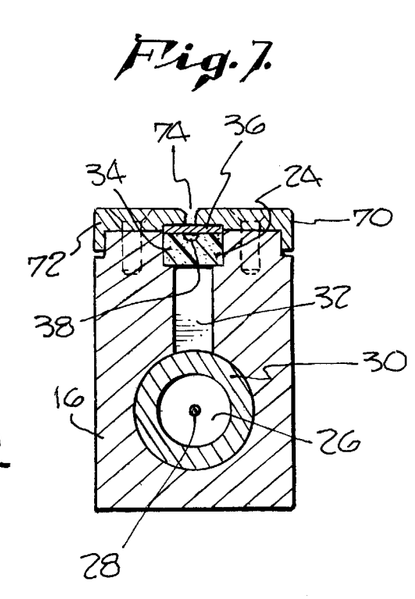
FIG. 7 is a side sectional view of FIG. 6 taken in the 7—7 plane.
Figure 8:
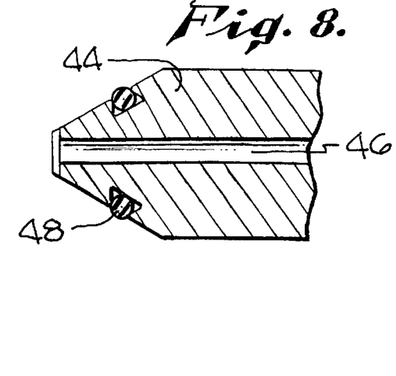
FIG. 8 is a detailed view of the tip of a preferred exemplary fill pin in accordance with the present invention.

The liquid permeable gel support bar 34 is preferably made from a liquid permeable plastic material. In accordance with the present invention, the liquid permeable gel support bar 34 includes a longitudinal depression in the surface which supports the gel. This longitudinal depression forms a channel 38, as best shown in FIG. 7, which allows various chemicals to be introduced into contact with the gel 36 prior to, during and/or after electrophoresis.

The first dimension housing 16 includes an opening 40 in the upstream end and an opening 42 in the downstream end. The two openings 40 and 42 are provided to allow introduction of various chemicals and reagents into channel 38 and to provide a location for connection of the first dimension electrophoresis electrodes as well as openings through which the electrophoresis gel and samples are introduced into the electrophoresis zone 24.

In accordance with the present inventory various pins are designed for insertion into the upstream and/or downstream openings 40 and 42 to provide for introduction of the necessary reagents and samples into the first dimension electrophoresis zone 24. The various pins are shown in FIGS. 6, 8, 9, 10 and 11.

Figure 6:
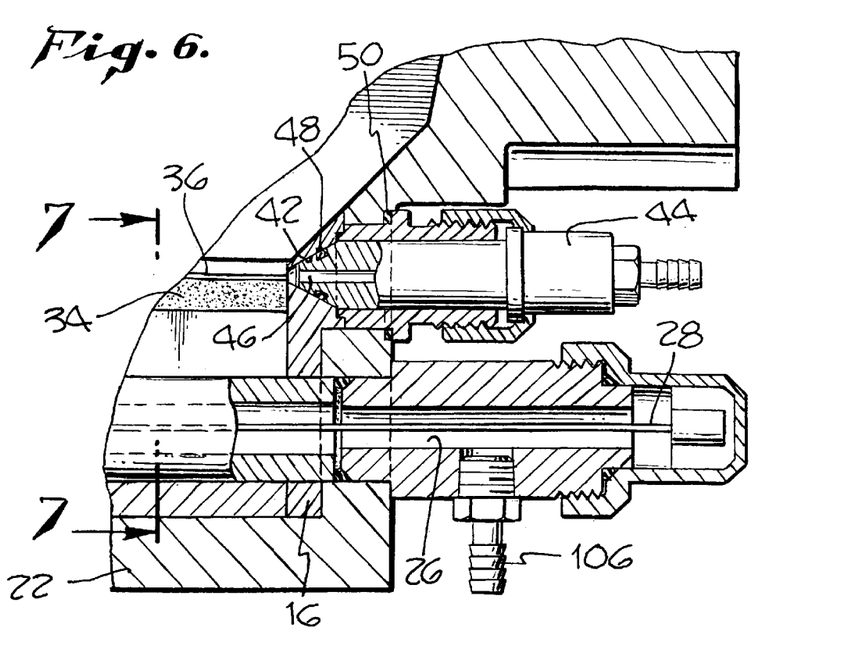
FIG. 6 is a detailed view of a portion of the preferred two dimensional electrophoresis apparatus of the present invention shown in FIG. 3.

Referring to FIG. 6, a fill pin 44 is shown inserted into position within opening 42. The fill pin 44 includes an interior channel 46 through which various gel precursors, reagents and other chemical solutions are introduced into the first dimension electrophoresis zone 24. An O-ring 48 is provided for insuring a liquid tight seal between the fill pin 44 and the housing opening. Preferably, a secondary seal is also provided by O-ring 50. In order to provide controlled introduction of materials into the first dimension electrophoresis zone 24, it is preferred that a second fill pin 52 (see FIG. 3) is provided on the opposite end of the first dimension housing 16.

As is well known, electrophoresis electrodes must be placed at opposite ends of the first dimension electrophoresis gel in order to conduct IEF or other electrophoretic procedure. An electrode assembly in accordance with the present invention is shown at 54 in FIG. 10. The electrode assembly 54 is shown in position within the downstream opening 42 in the first dimension housing 16. During electrophoresis, a second electrode assembly (not shown) is inserted into the upstream opening 40. The electrode assembly 54 includes an outer attach pin or banana jack 56 to which electrical leads from the power source are connected. The electrode assembly includes electrode 58 which is preferably a platinum wire. Other electrophoretic electrode types made from different materials may be used if desired.

Figure 10:
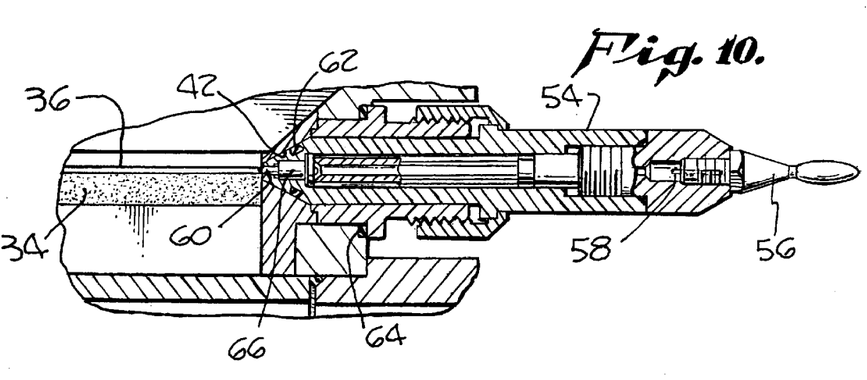
FIG. 10 is a sectional view of a preferred exemplary electrode assembly which includes a sample applicator tip for applying sample to the first dimension electrophoresis gel.
Figure 11:
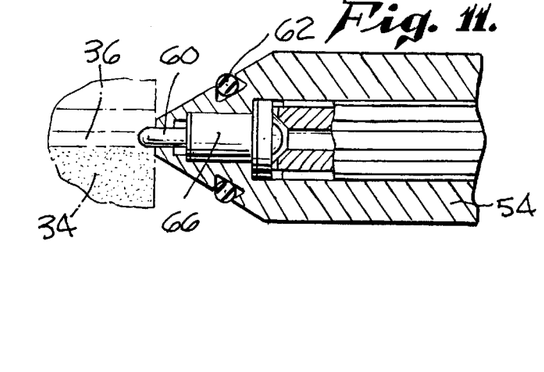
FIG. 11 is a detailed view of the sample applicator tip shown in FIG. 10.

In accordance with the present invention, a porous sample applicator tip 60 is provided in the electrode assembly 54 for applying a sample to the first dimension electrophoresis gel 36. The tip 60 is preferably spring loaded within the electrode assembly 54 so that it remains biased against the gel 36 to provide transfer of sample to the electrophoresis gel without actually penetrating into the gel. O-rings 62 and 64 are provided for insuring a fluid tight seal between the electrode assembly 54 and the housing 16. The porous sample tip 60 is housed within a sample tip holder 66. When sample application is not required, as in the case of the downstream electrode assembly, the sample pin 60 is removed from sample pin holder 66. Otherwise, the upstream and downstream electrode assemblies are preferably the same. Other electrode assemblies may be used provided that they are suitable for use in isoelectric focusing or other electrophoresis processes and are capable of being mounted to openings 40 and 42.

The first dimension electrophoresis box assembly 12 is connected to the second dimension box assembly 14 as best shown in FIG. 4 generally at 68. Plates 70 and 72 (also see FIG. 7) are mounted to the first dimension housing 16 so that a longitudinal gap 74 extends longitudinally next to the first dimension electrophoresis gel 36. This gap allows for direct contact between the second dimension electrophoresis gel 76 and the first dimension electrophoresis gel 36. The direct contact between the two gels in gap 74 allows for direct electrophoretic migration of the sample bands from the first dimension electrophoresis gel 36 into the second dimension electrophoresis gel 76.

The second dimension electrophoresis gel 76 is supported on both sides by gel support plates 78 and 80. The gel support plates 78 and 80 provide gel support surfaces which are positioned with respect to the first dimension electrophoresis gel support bar 34 to render the two gels coplanar to thereby allow direct electrophoretic migration of the sample bands from the first dimension electrophoresis gel 36 to the second dimension electrophoresis gel 76. The plates 76 and 78 are housed within a second dimension housing 82. The housing 82 and gel 76 have an upfield end shown generally at 84 and a downfield end shown generally at 86.

The electrodes which are utilized in the second dimension electrophoresis are shown at 28 and 90. As previously described, the electrode 28 is located in the second dimension electrophoresis electrode chamber 26 which is inside the first dimension housing 16. The electrode 28 along with porous plastic tube 30 are located on the upfield side of the first dimension gel 36 in order to provide the necessary electric field to electromigrate the sample bands from the first dimension gel 36 into the second dimension gel 76. The downfield electrode 90 is also surrounded by a porous plastic tube 92. The electrode 90 and tube 92 are mounted within a plastic mounting block 94 which is sealed to the support plates 78 and 80 by way of O-ring 96. The mounting block 94 is held in place by fasteners 98 and 100 (see FIG. 4).

A buffer inlet 102 and buffer outlet 104 are provided to allow introduction of suitable electrophoresis buffers into contact with the downfield electrode 90. Buffer inlet 106 and buffer outlet 108 are provided for introduction of suitable electrophoresis buffers into contact with the upfield electrode 28 (see FIG. 3).

The gel 76 used in the second dimension electrophoresis is preferably polyacrylamide which is conventionally used for SDS-PAGE electrophoresis. Other conventional electrophoresis gels may be utilized in the second dimension box assembly. The temperature of the second dimension electrophoresis gel is controlled by coolers 110 and 112. Any conventional cooling mechanism may be used which is capable of removing heat from the electrophoresis gel during second dimension electrophoresis, the coolers 110 and 112 are preferably electrically operated cooling units; however, cooling units based on the circulation of cooling fluid may also be used.

Referring to FIG. 3, gel inlet 114 and gel outlet 116 are provided for introducing gel precursors into the second dimension electrophoresis zone 118 to form appropriate gels between plates 78 and 80. During second dimension electrophoresis, the sample bands from the first dimension electrophoresis gel 36 travel from the upfield end of the second dimension housing to the downfield end of the second dimension housing. Preferably, the lateral width of the second dimension electrophoresis gel is greater than the length of the first dimension electrophoresis gel so that any edge effects associated with the second dimension electrophoresis are substantially eliminated. Referring to FIG. 3, this feature is depicted by the phantom lines 120 and 122 which show that the effective field for electromigration of the sample bands present in the first dimension gel 36 are limited to the area between the phantom lines 120 and 122 and that these lines are displaced significantly inward from the edge of the second dimensional electrophoresis gels at 1 24 and 126, respectively. As a result, any possible edge effects are eliminated or at least substantially reduced.

Electrical connectors such as banana jacks 128 and 130 are provided for connecting the upfield second dimension electrode 28 and downfield second dimension electrode 90, respectively to suitable electrophoresis power supplies conventionally used in SDS-PAGE electrophoresis and the like.

Figure 9:
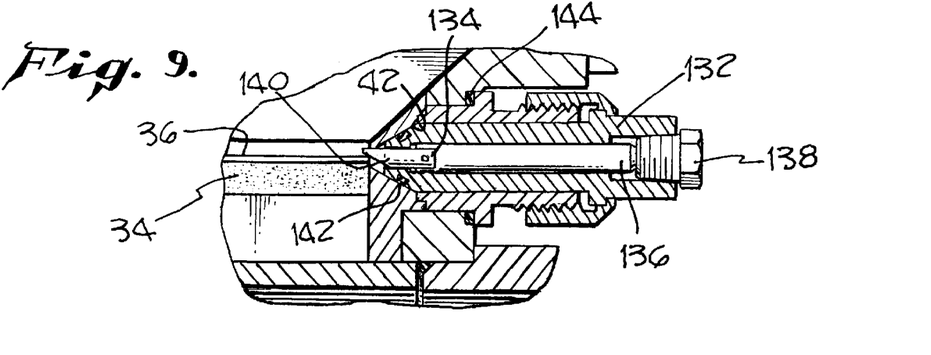
FIG. 9 is a sectional view showing a preferred exemplary pin for introducing a standard sample for use in the second dimension electrophoresis.

In conducting the second dimension electrophoresis, it is preferred that one or more standard samples be applied to the upstream or downstream end of the first dimension electrophoresis gel so that known band patterns will form along the edge of the second dimension electrophoresis field 120 and/or 122. In accordance with the present invention, an applicator pin for introducing a standard sample into the upstream or downstream end of gel 36 is shown in FIG. 9 at 132. The standard applicator pin 132 includes a porous tip 134 in which the standard sample is absorbed. The standard application tip 134 is mounted to rod 136 which is held in place by threaded cap 138. The porous standard sample tip 134 is shaped as shown at 140 so that it touches the first dimension gel only at the upper corner of the gel end. O-rings 142 and 144 are provided for insuring a fluid tight seal between the pin 132 and the housing opening 42. During second dimension electrophoresis when a voltage is applied between upfield electrode 28 and downfield electrode 90, the standard sample migrates from the first dimension electrophoresis gel into the second dimension electrophoresis gel and migrates downfield along phantom lines 120 and/or phantom line 122.

The first dimension housing 14 is held in place by plastic block 151 which is in turn held in place by fasteners 150 and 152 (see FIG. 4). If desired, multiple first dimension assemblies may be used to conduct electrophoresis on a plurality of samples. The resulting plurality of first dimensional electrophoresis assemblies can then be connected in sequence to the apparatus for sequential second dimension electrophoresis. After second dimension electrophoresis, both the first dimension gel and second dimension electrophoresis gel are removed. A new second dimension gel is introduced into the second dimension housing through inlet 114 and the next first dimension housing is clamped into position. If desired, the first dimension electrophoresis may be carried out prior to connection of the first dimension housing to the second dimension housing. In this instance, the plates 70 and 72 used during the initial first dimensional electrophoresis should not have gap 74. Instead, a solid plate is used. The solid plate is removed prior to connection of the first dimension housing to the second dimension housing and replaced with plates 70 and 72 to provide the gap 74 for gel contact between the first dimension gel and second dimension gel.

Figure 12:
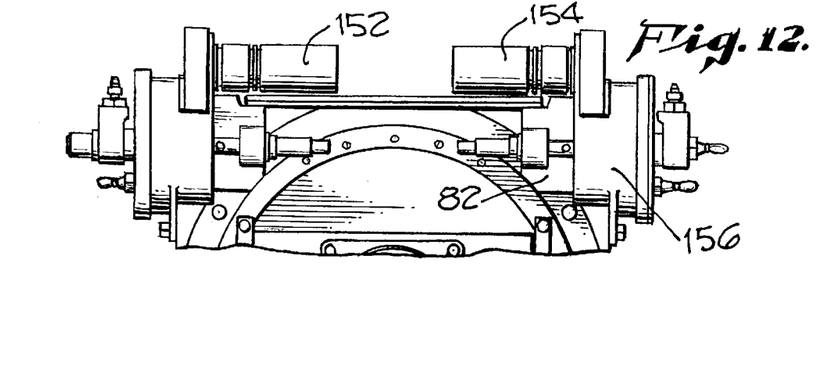
FIG. 12 is a partially schematic representation of an automatic sequencing device for use in sequentially presenting first dimension electrophoresis housings into position with respect to the second dimension electrophoresis box assembly for initiation of second dimension electrophoresis.

If desired, an automatic feeder assembly may be used to automatically feed the first dimension housing assemblies into position for second dimension electrophoresis. An exemplary automatic feed system is shown in FIG. 12. The system includes actuator motors 152 and 154 which may be selectively actuated to rotate first dimension housings located in carousel 156 into appropriate alignment with the second dimension housing. Other arrangements for sequentially feeding a plurality of first dimension housings into engagement with the second dimension housing are possible provided that they insure a coplanar contact between the two gels so that electromigration of sample bands from the first dimension gel into the second dimension gel is uniformly accomplished along the entire length of the first dimension gel.

The materials used in fabricating the apparatus of the present invention may be any of the plastic, glass, ceramic and/or metal materials conventionally used in fabricating electrophoresis gel boxes. Where possible, it is preferred that plastic materials be utilized due to their insulative characteristics, relative biological inertness and resistance to corrosion.

Having thus described exemplary embodiments of the present invention, it will be understood by those skilled in the art that the within disclosures are exemplary only and that various other alternatives, adaptations, and modifications may be made within the scope of the present invention. Accordingly, the present invention is not limited to the specific embodiments as illustrated herein.

What is claimed is:

1. An apparatus for conducting two dimensional electrophoresis of a sample, said apparatus comprising:

A) a first dimension electrophoresis box assembly comprising:

1) a first dimension housing comprising an upstream end at which said sample is located prior to first dimension electrophoresis and a downstream end toward which said sample migrates during electrophoresis, said first dimension housing further comprising interior walls which define a longitudinal first dimension electrophoresis zone which extends from said upstream end of said first dimension housing to said downstream end, said first dimension housing further comprising interior walls which define a second dimension electrophoresis electrode chamber which extends longitudinally parallel to said first dimension electrophoresis zone, wherein said first dimension electrophoresis zone is in fluid communication with said second dimension electrophoresis electrode chamber;

2) a liquid permeable gel support bar located in said first dimension electrophoresis zone and extending from said upstream end to said downstream end, said gel support bar including a first dimension electrophoresis gel support surface upon which a first dimension electrophoresis gel may be supported, said gel support surface comprising a longitudinal depression in said surface which defines a channel through which fluids may be introduced for interaction with a gel located on said first dimension electrophoresis gel support surface;

3) means for connecting an upstream electrophoresis electrode to the upstream end of said first dimension housing so that said upstream electrode is in fluid communication with said first dimension electrophoresis zone;

4) means for connecting a downstream electrophoresis electrode to the downstream end of said first dimension housing so that said downstream electrode is in fluid communication with said first dimension electrophoresis zone, wherein during first dimension electrophoresis, said sample is separated into first dimension sample bands within said first dimension electrophoresis gel, said first dimension sample bands being present at spaced locations between said upstream and downstream ends of the first dimension housing;

B) a second dimension electrophoresis box assembly comprising:

1) a second dimension housing comprising an upfield end located adjacent to said first dimension housing and a downfield end towards which the sample bands migrate during second dimension electrophoresis, said second dimension housing further comprising interior walls which define a second electrophoresis zone which extends from the upfield end of said second dimension housing to said downfield end, wherein said interior walls of said second dimension housing include at least one second dimension electrophoresis gel support surface for supporting an electrophoresis gel for conducting second dimension electrophoresis of said sample bands, said second dimension electrophoresis gel support surface extending laterally from the upstream end of said first dimension housing to the downstream end of said first dimension housing and extending longitudinally from the upfield end of said second dimension housing to the downfield end of said second dimension housing;

2) a second dimension downfield electrophoresis electrode located at the downfield end of said second dimension housing;

3) a second dimension upfield electrode located in said second dimension electrophoresis electrode chamber which is located in said first dimension housing, wherein during second dimension electrophoresis, said first dimension sample bands from said first dimension electrophoresis migrate towards said downfield electrophoresis electrode and are each separated into second dimension sample bands; and C) connection means for connecting said first dimension electrophoresis box assembly to said second dimension electrophoresis box assembly so that said first dimension electrophoresis gel support surface is positioned relative to said second dimension electrophoresis gel support surface so that the first dimension gel and second dimension gel are coplanar whereby said first dimension sample bands present in the first dimension electrophoresis gel may be transferred by electrophoretic migration to the second dimension electrophoresis gel for second dimension electrophoresis.

2. An apparatus for conducting two dimensional electrophoresis according to claim 1 which further comprises second dimension temperature control means for controlling the temperature within said second dimension electrophoresis zone.

3. An apparatus for conducting two dimensional electrophoresis according to claim 2 which further comprises first dimension temperature control means for controlling the temperature within said first dimension electrophoresis zone.

4. An apparatus for conducting two dimensional electrophoresis according to claim 1 wherein said means for connecting said upstream electrophoresis electrode to said first dimension housing comprises an upstream opening in said first dimension housing into which an upstream eletrophoresis electrode assembly may be inserted, said apparatus further comprising an upstream electrophoresis electrode assembly for insertion into said upstream opening and means for providing a fluid tight seal between said upstream electrophoresis electrode assembly and said first dimension housing when said upstream electrophoresis electrode assembly is inserted within said upstream opening.

5. An apparatus for conducting two dimensional electrophoresis according to claim 4 wherein said upstream electrode assembly comprises means for applying a sample to an electrophoresis gel located in said first dimension electrophoresis zone.

6. An apparatus for conducting two dimensional electrophoresis according to claim 4 wherein said apparatus further comprises an upstream fill pin which is insertable within said upstream opening, said upstream fill pin comprising an interior channel through which fluids may be introduced into said first dimension electrophoresis zone and means for providing a fluid tight seal between said upstream fill pin and said first dimension housing when said upstream fill pin is located within said upstream opening.

7. An apparatus for conducting two dimensional electrophoresis according to claim 4 wherein said apparatus further comprises an upstream second dimension standard pin which is insertable within said upstream opening, said upstream standard pin comprising means for applying a standard sample band to the upstream end of a first dimension electrophoresis gel whereby said standard sample band will migrate along the upstream lateral side of a second dimension electrophoresis gel located on said second dimension electrophoresis gel support surface during second dimension electrophoresis.

8. An apparatus for conducting two dimensional electrophoresis according to claim 1 wherein said means for connecting said downstream electrophoresis electrode to said first dimension housing comprises a downstream opening in said first dimension housing into which a downstream electrophoresis electrode assembly may be inserted, said apparatus further comprising a downstream electrophoresis electrode assembly for insertion into said downstream opening and means for providing a fluid tight seal between said downstream electrophoresis electrode assembly and said first dimension housing when said downstream electrophoresis electrode assembly is inserted within said downstream opening.

9. An apparatus for conducting two dimensional electrophoresis according to claim 8 wherein said downstream electrode assembly comprises means for applying a sample to an electrophoresis gel located in said first dimension electrophoresis zone.

10. An apparatus for conducting two dimensional electrophoresis according to claim 8 wherein said apparatus further comprises a downstream fill pin which is insertable within said downstream opening, said downstream fill pin comprising an interior channel through which fluids may be introduced into said first dimension electrophoresis zone and means for providing a fluid tight seal between said downstream fill pin and said first dimension housing when said downstream fill pin is located within said downstream opening.

11. An apparatus for conducting two dimensional electrophoresis according to claim 8 wherein said apparatus further comprises a downstream second dimension standard pin which is insertable within said downstream opening, said downstream standard pin comprising means for applying a standard sample band to the downstream end of a first dimension electrophoresis gel whereby said standard sample band will migrate along the downstream lateral side of a second dimension electrophoresis gel located on said second dimension electrophoresis gel support surface during second dimension electrophoresis.

12. An apparatus for conducting two dimensional electrophoresis according to claim 1 wherein said fluid communication between said first dimension electrophoresis zone and said second dimension electrophoresis electrode chamber is connected by a channel extending between said zone and said chamber wherein said channel extends longitudinally from the upstream end of said first dimension housing to the downstream end thereof.

13. An apparatus for conducting two dimensional electrophoresis according to claim 1 wherein said means for connecting said first dimension electrophoresis box assembly to said second dimension electrophoresis box assembly comprises a gel opening in said first dimension housing and a gel opening in said second dimension housing wherein said openings are shaped for sealing contact between said first and second dimension housings to provide for contact of the first and second dimension electrophoresis gels located therein so that the first dimension sample bands present in the first dimension electrophoresis gel may migrate by electrophoresis to the second dimension electrophoresis gel.

14. An apparatus for conducting two dimensional electrophoresis according to claim 1 wherein said second dimension electrophoresis box assembly further comprises fill means for loading said second dimension electrophoresis zone with gel precursors used in forming the second dimension electrophoresis gel.

15. An apparatus for conducting two dimensional electrophoresis according to claim 1 wherein said apparatus comprises a plurality of first dimension electrophoresis box assemblies and wherein said connection means for connecting said first dimension electrophoresis box assembly to said second dimension electrophoresis box assembly comprises sequence means for sequentially connecting said plurality of first dimension electrophoresis box assemblies to said second dimension box assembly.

* * * * *